United States Patent [19]

Galanos et al.

[11] 4,029,762

[45] June 14, 1977

[54] LIPID A-PREPARATION

[75] Inventors: Chris Galanos; Otto Lüderitz; Otto Westphal, all of Freiburg, Germany

[73] Assignee: Max-Planck-Gesellschaft zur Forderung der Wissenschaften e.V., Gottingen, Germany

[22] Filed: Dec. 22, 1975

[21] Appl. No.: 643,121

Related U.S. Application Data

[63] Continuation-in-part of Ser. No. 578,383, May 19, 1975, abandoned, which is a continuation of Ser. No. 306,022, Nov. 13, 1972, abandoned.

[30] Foreign Application Priority Data

Nov. 17, 1971 Germany .......................... 2157148

[52] U.S. Cl. .............................. 424/87; 260/112 R; 424/92

[51] Int. Cl.² ................ A61K 37/20; A61K 39/02; A61K 39/40

[58] Field of Search ................................ 424/87, 92

[56] References Cited

UNITED STATES PATENTS 3,185,624  5/1965  Nakazawa ........................... 424/92
3,652,761  3/1972  Weetall ........................... 424/87 X

OTHER PUBLICATIONS

Kamio et al., J. Biochem., vol. 70, pp. 187–191 (1971).
Thiersch, P.S.E.B.M., vol. 109, pp. 437–441 (1962).

Primary Examiner—Dolph H. Torrence
Attorney, Agent, or Firm—Curtis, Morris & Safford

[57] ABSTRACT

A preparation consisting essentially of lipid A or alkali-treated lipid A adsorbed on a particulate organic carrier material and an immunizing agent containing same being useful against diseases caused by gram-negative enterobacteriaceae.

16 Claims, No Drawings

LIPID A-PREPARATION

This application is a continuation-in-part application of application Ser. No. 578,383 filed May 19, 1975, now abandoned, which application in turn is a continuation application of application Ser. No. 306,022 filed on Nov. 13, 1972, now abandoned.

The present invention relates to a preparation suitable as an immunizing agent for bacterial infections, and particularly for infections caused by gramnegative enterobacteriaceae.

Many infectious diseases caused by enterobacteriaceae in humans and animals are produced by poisons which are only liberated during disintegration or decomposition of the bacteria. These poisons are called endotoxins. Immunity against diseases caused by endotoxins is based on the protective substances which the infected organism immediately produces against the bacteria causing the disease. In these cases, strictly specific substances, capable of rendering the infectious agent harmless by lump formation (agglutination) or decomposition (lysis), are present in the blood of the infected organism.

The course of an infection can be controlled by immunoprophylaxis or by immunotherapy.

The incorporation of isolated toxins, i.e. substances acting as antigen, or virulent pathogenic organisms for active immunization involves extensive processes. On the one hand, only specially prepared toxins can be used as vaccines and on the other, the individual vaccines only have a specific effect. Therefore, it is always necessary to select the suitable vaccine or the suitable serum. Thus, immunoprophylaxis against different pathogenic organisms requires the corresponding amount of vaccinations. Especially in the case of children, the question increasingly arises how such a large number of vaccinations can be made within the short period of the first years of life.

Further problems arise in the case of passive immunization with antisera. In the case of infectious diseases, it is often unknown which specific pathogenic organisms are the cause of the disease. When an antiserum is used to treat an infectious disease, the recipient is necessarily also given the serum albumin of the animal species from which the antiserum is prepared, together with the antitoxic serum obtained from the animal, and repeated use may cause failure of circulation, formation of edemas and the appearance of exanthemas. Therefore, it is advantageous to limit the number of injections when administering sera.

Consequently, there is a requirement for sera having a spectrum of effect which is as wide as possible.

From the above it follows that the hitherto known vaccines and sera are only effective against special serum types of the enterobacteriaceae and that for an effective immunoprophylaxis and immunotherapy it is often necessary to administer several vaccines and sera. This makes it necessary, in the case of an infection, to ascertain the serum type of the pathogenic organism and subsequently to produce and apply the corresponding vaccine. The use of combination vaccines and combination sera has already been suggested. However, this has the disadvantage that the antigens exert a mutual influence upon one another, for example a suppression of the vaccination reaction against a weak antigen by a stronger antigen or in the case of live vaccines by lack of infectivity of the pathologic organisms, or a mutual stimulation in the sense of an adjuvant effect. The administration of such combination preparations is therefore accompanied by difficulties.

It has been shown that lipopolysaccharides are located on the surface of bacteria.

Lipopolysaccharides may be extracted from smooth-form bacteria in accordance with the known phenol/-water process or from rough-form bacteria in accordance with the known phenol/chloroform/petroleum ether process. Lipopolysaccharides consist of a lipid portion which is bound to polysaccharides. Gram-negative bacteria contain on their surface lipopolysaccharides which are characterized by manifold biological activities. They are the O antigens of bacteria, are highly effective endotoxins and act as receivers for bacteriophages. By the injection of isolated lipopolysaccharide it is possible to produce many disease symptoms which appear in the case of infections. Their pyrogenic effect is particularly striking. Thus, for example, the injection of 1 $\mu$g of a lipopolysaccharide causes an attack of fever to 40° C after a short latency period in humans. Lipopolysaccharides cause many other biological reactions, e.g. the Schwartzmann phenomenon, tumor necrosis, blood pressure changes, fibrinolysis, changes in the resistance towards infections, adjuvant effects, etc. Therefore, the lipopolysaccharides of gramnegative bacteria are a remarkable large class of biologically interesting natural matter, having an effect as antigens, as endotoxins or as phage receivers. They are built up in accordance with a common structure principle and generally consist of 3 regions of different structure. Thus, all lipopolysaccharides contain a lipid component, lipid A (region III), to which are united the nucleus polysaccharide (region II) and O specific chains (region I).

In the parent applications Ser. Nos. 306,022 and 578,383 the lipid A is called "Lipoid A" due to an inadvertance of the translator. We prefer the more correct word "Lipid" which is the English translation of both German words Lipid and Lipoid which are used as synonyms in this language (cf. Reallexikon der Medizin pgs. L 132 and L134). The word Lipid is used in the present application in the same sense as Lipoid in the parent applications.

In nature there exist innumerable gram-negative species which are all based on the same structure principle, in which regions I and II show differences, but in all cases the lipid A is present as region III. This holds good for all gram-negative bacteria.

R mutant strains contain defective lipopolysaccharides. The O specific chains are not present and the nucleus polysaccharide is present in a more or less complete form, depending on the sites of mutation.

Immunization of animals with bacteria or isolated lipopolysaccharides leads to the formation of specific antilipopolysaccharide antibodies. They mainly involve determinants in the sugar portion of the molecule.

The production of Lipid A is effected by cultivating gram-negative enterobacteria in conventional manner and then killing the cultures. The bacteria may be isolated in known manner. The lipopolysaccharides are obtained from these bacteria and are then hydrolysed, in conventional manner, conveniently by using a dilute acid such as acetic acid, whereby lipid A is obtained.

As mentioned above, lipid A is the main component part of all lipopolysaccharides and is structurally identical in all enterobacteriaceae.

Alkali-treated lipid A appears to be of lesser toxicity than the unmodified lipid A. Alkali-treated lipid A may be prepared by a process comprising treating lipid A with sodium or potassium hydroxide. It is prefered to use sodium hydroxide, conveniently in dilute, e.g. 0.1 to 1N, aqueous solution, and it is preferred to carry out the process at a temperature from room temperature to about 90° C, especially 50° to 70° C. The alkali-treated lipid A is soluble and may be purified by methods conventional in the art.

The invention provides a preparation, consisting essentially of lipid A or alkali-treated lipid A physically absorbed on a carrier. The carrier, in general, is a particulate organic material having distinct hydrophilic and hydrophobic regions. Such organic materials are found in the nature e.g. in the form of bacteria shells or cell walls. They can also be synthesized as so called liposomes.

Liposomes are small particles comprising a series of lipid-layers spaced one from another by a lipophilic material, the outermost layer being lipid. They are wellknown to biological research workers. The carrier may also be non-pathogenic bacteria, such as non-hydrolysed or hydrolysed bacteria particularly gram-negative bacteria which are alive or have been killed, for example non-hydrolysed killed Salmonella or E. Coli bacteria, or may be an inert carrier, such as isolated bacterial cell walls, e.g. peptidoglycan.

For adsorption the lipid A or the alkali treated lipid A is contacted in an aqueous medium with the carrier material. The conditions are those generally applied in adsorption reactions.

Lipid A or alkali treated lipid A adsorbed on a carrier, and mixtures thereof with lipid A or alkali treated lipid A or anti-lipid A possess immunological activity in animals which is higher than the activity of the free lipid A or alkali treated lipid A. In particular, they are indicated as immunizating agents against diseases caused by gram-negative enterobactericeae, for example against typhoid and paratyphoid diseases, bacterial dysentery (Shigellosis), infantile coli-ente-ritis, infections with colibacillus and Salmonella enteritis. This is indicated by tests in groups of mice administered 0.06 mg/Kg of such a modified lipid A preparation and infected by massive doses of *E. Coli* or Salmonella enteritis and comparing survival times with a control group.

Immunizing agents comprising such modified lipid A preparations may be prepared in manner well known in the art, and may be used with conventional carriers or diluents and/or adjuvants. The dosage admininstered will vary according to the preparation used and the treatment desired.

In general, satisfactory results are obtained when such a modified lipid A preparation (lipid A or alkali-treated lipid A absorbed on a carrier) is administered as antigen at a dosage of about 0.015 to 0.06 mg/Kg animal body weight; The dosage may be given in a single dose or in up to four divided doses. For the larger mammals, the total dosage on one day is about 1 to 4 mg, and divided doses suitable for i.v. administration comprise from about 0.25 to 2 mg in admixture with a diluent or carrier suitable for injection.

The preparation can also be used for the isolation of lipid A-antibodies by way of immuno adsorption. Thus a lipid A or an alkali treated lipid A adsorbed on a carrier is contacted with an aqueous liquid containing a lipid A antibody e.g. a blood serum of a test animal treated with lipid A. The preparation on which the antibody is adsorbed is separated from the liquid in a usual manner e.g. by centrifugation and the antibody is recovered by desorbing it from the preparation. Desorption of the antibody is preferably carried out by dispersing the preparation in a buffer solution the pH of which is in the range between 1 and 4 and separating the aqueous phase containing the antibody.

Lipid A antibodies can be obtained in conventional manner by using lipid A or alkali-treated lipid A adsorbed on a carrier e.g. bacteria coated with lipid A. Suitable mammals are rabbits, which may be administered a total of about 100 $\mu$ to 2 mg, and the antiserum extracted from blood taken some two to five weeks after administration of the antigen. The antiserum isolated from the blood of the animals may be used directly for prophylaxis and therapy of diseases caused by gram-negative enterobacteriaceae.

The following Examples illustrate the invention but in no way limit its scope.

1. Lipid A

Free lipid A is obtained by hydrolysis of the corresponding lipopolysaccharide in a dilute acid, e.g. in 1% acetic acid, at 100° C for 2 hours. The water-insoluble free lipid A is washed several times with distilled water and dried in a vacuum. No 2-keto-3-desoxyoctonate (KDO) can be ascertained in such preparations. Lipid A can be solubilized by the addition of triethylamine (1 $\mu$l) to a suspension of lipid A in water (2mg/2ml). Other amines and other basic-reacting substances may likewise be used for the solubilization of lipid A.

2. Alkali-treated lipid A

Free lipid A is heated at 56° C for 1 hour in 0.25 normal sodium hydroxide. The insoluble material is removed, and the supernatant liquid is neutralized with acetic acid, whereby a precipitate is formed. The precipitate is removed and the supernatant solution is dialyzed against distilled water. The precipitated material is again removed by centrifuging and the supernatant liquid, which contains soluble, alkali-treated lipid A, is freeze-dried.

3. Bacteria coated with lipid A

Bacteria coated with lipid A are produced by suspending lipid A in distilled water (1 mg/ml) and solubilizing by the addition of triethylamine (1 $\mu$ 1/2 ml). Aliquot parts of these solutions are mixed with 2 ml of a suspension of the bacteria in distilled water (1 mg/2 ml) and the mixture is then dried. In this manner bacteria are obtained which are coated with 10, 100 or 500 $\mu$ g of lipid A for every mg of dry weight.

Hydrolyzed bacteria are coated with lipid A in similar manner. For hydrolysis, the dried bacteria are washed twice with 1% acetic acid, are then suspended in 1% acetic acid (1 g/50 ml) and are heated at 100° C for 2 hours. They are then washed with distilled water, dried in a vacuum and coated with lipid A as described above.

4. Production of lipid A Antibodies

White New Zealand Rabbits with a body weight from 2 to 2.5 Kg are administered lipid A by intravenous injection in four different amounts:

| | |
|---|---|
| 1st day | 100 $\mu$g |
| 3rd day | 200 $\mu$g |
| 7th day | 300 $\mu$g |
| 11th day | 500 $\mu$g |

On the 16th day blood is taken from the animals by heart puncture and is further worked up in conventional manner to isolate the lipid A antiserum.

The antiserum may also be produced by injection champagne-coloured silver rabbits of body weight 1.5 Kg with a total of 1.5 mg of lipid A in 1 ml of incomplete Freund's adjuvant, subcutaneously in four different injection sites.

The injections are repeated 7 weeks later and 10 days thereafter blood is taken from the animals from the ear vein and worked up in conventional manner.

Erythrocytes, which have been sensitized either with lipid A or with alkali-treated lipid A, essentially give the same results. For purposes of simplification, alkali-treated lipid A is generally used to coat the erythrocytes.

Lipid A antiserum (1 ml) is mixed with packed red cells treated with formalin (0.1 ml), which have been sensitized with alkali-treated lipid A (100 μg). The mixture is stirred at room temperature for 15 minutes and the cells are then separated by centrifuging.

For purposes of desorption of the lipid A antibodies, the cells are stirred, after absorption, in a 0.1 molar glycine/HCl buffer (pH 2.2) 2 ml, at room temperature for one hour. After centrifuging, the supernatant liquid is neutralized with sodium hydroxide and concentrated to the original volume (1 ml) by ultrafiltration.

The resulting lipid A and the lipid A preparations are used in the following tests. In the tests indicated below, untreated bacteria and lipid A-covered bacteria are used as antigens. Furthermore, in control tests, fresh bacteria killed with heating are used as antigens and incomplete Freund's adjuvant is used alone. Antibacterial sera against S and R form bacteria are produced.

Antilipid A activity of various antisera.

In order to determine the antilipid A activity in the corresponding serum, the passive hemolysis test is carried out, whereby red blood cells, which have been coated with alkali-treated lipid A from S. minnesota R345, are used. Subcutaneous immunization in incomplete Freund's adjuvant generally leads to a slightly higher antilipid A titer as compared with the intravenous immunization scheme.

Both processes give the best results when hydrolyzed S. Minnesota R595 bacteria coated with lipid A are used as antigen. Good results are likewise obtained when immunization is effected with hydrolyzed bacteria or with non-hydrolyzed bacteria coated with lipid A. Immunization with bacteria killed either with phenol or with heat leads to lower values of the antilipid A activity. No antibodies can be ascertained in the pre-blood serum or after injection with incomplete Freund's adjuvant.

Specific absorption and desorption of lipid A antibodies

The specificity of a lipid A antiserum is tested by absorption with formalin-treated erythrocytes which are sensitized with lipid A (from S. Minnesota R345).

The absorbed serum has no antilipid A activity, whereas in the comparison test (treatment with non-sensitized erythrocytes) no titer decrease is observed.

The absorbed lipid A antibodies may be dissociated by incubating the cells coated with lipid A, with glycine/HCl buffer at pH 2.2. A considerable amount of the antilipid A activity is recovered.

Serological cross reactiion between lipid A and various lipopolysaccharides of the S and R forms The capacity of lipid A antiserum to react with S and R lipopolysaccharides of Salmonella and E. coli strains, is examined in the passive hemolysis test with red cells which are sensitized with these preparations. All S and R forms of lipopolysaccharides react with the antilipid A serum. In order to prove the specificity of these cross reactions, the lipopolysaccharides of various bacteria are tested with the same serum after absorption with lipid A. In no case does a cross reaction take place.

What we claim is:

1. A preparation consisting essentially of a member selected from the group consisting of lipid A and alkali-treated lipid A adsorbed on a water-insoluble particulate organic carrier material having distinct hydrophilic and hydrophobic regions.

2. A preparation as in claim 1, wherein the carrier material is selected from the group consisting of erythrocytes, live apathogenic bacteria, killed bacteria, the cell-walls of killed bacteria and liposomes.

3. A preparation as in claim 1, wherein the carrier is dispersed in an aqueous medium.

4. A preparation as in claim 1, wherein said carrier is erythrocytes.

5. A preparation as in claim 1, wherein said carrier is the cell-walls of killed bacteria.

6. A preparation as in claim 1, wherein said carrier is gram-negative bacteria or the cell-walls thereof.

7. A preparation as in claim 6, wherein said bacteria are selected from the group consisting of Salmonella and coli bacteria.

8. A preparation as in claim 1, wherein said carrier is a liposome.

9. An immunizing agent consisting essentially of the preparation of claim 1 in an effective amount suitable for injection.

10. An immunizing agent as in claim 9, wherein said carrier is erythrocytes.

11. An immunizing agent as in claim 9, wherein said carrier is the cell-walls of killed bacteria.

12. An immunizing agent as in claim 9, wherein said carrier is gram-negative bacteria or the cell walls thereof.

13. An immunizing agent as in claim 12, wherein said bacteria are selected from the group consisting of Salmonella and coli bacteria.

14. An immunizing agent as in claim 9, wherein said carrier is a liposome.

15. A method for isolating a lipid A antibody which comprises contacting a preparation as claimed in claim 1 with an aqueous liquid containing such an antibody, separating the preparation on which said antibody is adsorbed and desorbing the anti-body therefrom.

16. The method of claim 15, wherein for desorption the preparation is treated with a buffer solution of pH 1–4.

* * * * *